(12) United States Patent
Seed et al.

(10) Patent No.: US 7,109,206 B2
(45) Date of Patent: *Sep. 19, 2006

(54) METHODS AND COMPOSITIONS FOR THE RAPID AND ENDURING RELIEF OF INADEQUATE MYOCARDIAL FUNCTION

(75) Inventors: Brian Seed, Boston, MA (US); John C. Seed, Princeton, NJ (US)

(73) Assignee: Heart Care Partners, Princeton, NJ (US)

( * ) Notice: Subject to any disclaimer, the term of this patent is extended or adjusted under 35 U.S.C. 154(b) by 1115 days.

This patent is subject to a terminal disclaimer.

(21) Appl. No.: 09/735,024

(22) Filed: Dec. 12, 2000

(65) Prior Publication Data

US 2002/0016312 A1   Feb. 7, 2002

Related U.S. Application Data

(63) Continuation of application No. 09/198,874, filed on Nov. 24, 1998, now Pat. No. 6,159,993, which is a continuation of application No. 08/680,684, filed on Jul. 17, 1996, now Pat. No. 5,861,399.

(51) Int. Cl.
*A61K 31/505* (2006.01)
*A61K 31/44* (2006.01)
*A61K 31/40* (2006.01)
*A61K 31/35* (2006.01)
*A61K 31/21* (2006.01)

(52) U.S. Cl. ............ 514/275; 514/356; 514/419; 514/460; 514/510; 424/523

(58) Field of Classification Search ........ 514/510, 514/460, 419, 356, 275, 165, 167; 424/523
See application file for complete search history.

(56) References Cited

U.S. PATENT DOCUMENTS 5,800,385 A * 9/1998 Demopulos et al.
5,861,399 A * 1/1999 Seed et al. ............ 514/252.15
6,159,993 A * 12/2000 Seed et al. ............... 514/356

OTHER PUBLICATIONS

Sassen et al., Cardiovasc. Drugs ther., 1994; 8(2):179-191.*
Vane et al., Circulation, 1991; 84(6):2588-2590.*
Lee et al., Am. J. Cardiol., 1994; 73(15):1037-1040.*
Watts et al., Lancet, 1992; 339(8793):563-569.*
Conn's Current Therapy 1992. W.B. Saunders Co., Phil. PA, pp. 205-207, 279-281 (1992).
Brelvik et al., CA 107:156946 (1987).

* cited by examiner

Primary Examiner—San-ming Hui
(74) Attorney, Agent, or Firm—Clark & Elbing LLP

(57) ABSTRACT

Disclosed are methods and compositions for reducing coronary artery stenosis, restoring blood flow to infarcted myocardium, improving myocardial perfusion, reducing heart attacks or other adverse cardiovascular events, or treating symptoms of inadequate myocardial function in a mammal involving administering to the mammal (a) a compound that includes eicosapentaeneoic acid or docosahexaeneoic acid and (b) a cholesterol-lowering therapeutic, combined with dietary restrictions (resulting in aggressive loading of marine lipids), whereby a serum LDL concentration of less than 75 mg/dl (and preferably less than 55 mg/dl) is achieved. One particular method involves administering to the mammal a combination that includes (a) a compound that includes an eicosapentaeneoic or docosahexaeneoic acid (for example, a marine lipid) and (b) a cholesterol synthesis or transfer inhibitor, and which may also optionally include aspirin and/or niacin. The methods and compositions of the invention may also further include a bile acid sequestrant and/or buspirone. Also disclosed are methods for treating heart disease that involve administration of buspirone.

17 Claims, No Drawings

METHODS AND COMPOSITIONS FOR THE RAPID AND ENDURING RELIEF OF INADEQUATE MYOCARDIAL FUNCTION

This application is a continuation of U.S. Ser. No. 09/198, 874, filed Nov. 24, 1998, now U.S. Pat. No. 6,159,993, which is a continuation of U.S. Ser. No. 08/680,684, filed Jul. 17, 1996, now U.S. Pat. No. 5,861,399.

BACKGROUND OF THE INVENTION

This invention relates to methods and compositions for rapid and enduring improvement in blood flow to the heart and for the prompt relief of inadequate myocardial function.

This invention is a continuation of U.S. Ser. No. 08/680, 684, filed Jul. 17, 1996.

Angina pectoris, the syndrome of chest pain or tightness commonly elicited by exertion or emotional stress, and occasionally appearing in the absence of provocation (as unstable angina), is caused by inadequate blood flow through the coronary arteries. The subsequent deprivation of oxygen (ischemia) to the myocardium triggers pain and discomfort by an unknown mechanism. Appearance of angina in an otherwise well patient is of medical concern because it indicates the presence of an obstructive lesion or partial stenosis of one or more coronary arteries, usually as the result of the buildup of atherosclerotic plaque. Angina is often taken to be an indication for the initiation of one form or another of invasive cardiac revascularization, such as percutaneous transluminal angioplasty (PCTA), or cardiac artery bypass grafting (CABG). Both therapies carry significant intraprocedural risk and the failure rate, as measured by the need for repetition, can be significant.

One benefit of revascularization is palliation of the symptoms of angina. Of considerable concern to the patient, the onset of chest pain and/or tightness reinforces an awareness of the fragility of their existence. The resulting concern about and avoidance of activities which may provoke further symptoms can lead to a debilitating preoccupation with morbidity and restriction of daily activities. In many cases the principal benefit of invasive revascularization may be relief of the symptoms of angina.

The proximate cause of angina, narrowing of the coronary arteries, is the outcome of a slowly evolving progressive stenosis of the artery lumen by atherosclerotic plaque and spasm of the artery in the vicinity of the plaque. Many factors contribute to the development of plaque and spasm, including high levels of certain plasma lipoproteins, cigarette smoking, hypertension, heritable risk factors, and the contributions of noncardiovascular diseases such as diabetes. An important constituent of plaque is cholesterol, and hypercholesterolemia is an important risk indicator.

Medical treatment of hypercholesterolemia over an extended period of time has been shown to result in objective widening of the lumen of arteries narrowed by atherosclerosis. The benefits of medical treatment are generally not rapid, however, and prompt and enduring improvement in myocardial function, with concurrent rapid symptomatic relief of the pain and discomfort of angina has not been reported in the medical literature.

At present, angina is treated medically by the use of nitrates, principally nitroglycerin and isosorbide dinitrate, which promote vascular perfusion by serving as a reservoir from which the endothelial relaxing factor, nitric oxide, can be formed. Although nitrates provide relief, their short duration of action and relatively constrained ability to prevent new episodes, in certain respects, limit their utility. Moreover, treatment of angina with nitrates does not induce an enduring improvement in cardiovascular status. Also, long term exposure to nitrates may result in thickening of coronary musculature and an increased tendency toward myocardial infarction.

Although the literature contains many references to the use of one or several of the medication components described herein, there has been no description to date of a treatment program which combines aggressive cholesterol lowering with marine lipid loading. This combination is shown here to promote rapid and enduring improvement in myocardial function.

SUMMARY OF THE INVENTION

In a first aspect, the invention features a method for treating inadequate myocardial function in a mammal that involves administering to the mammal a combination including (a) a compound that includes eicosapentaeneoic acid or docosahexaeneoic acid (for example, a marine lipid) and (b) a cholesterol synthesis or transfer inhibitor, in combination with dietary restrictions, whereby a serum LDL concentration of less than or equal to 70 mg/dl is achieved and whereby the treatment results in a rapid and enduring reduction in a symptom of inadequate myocardial function. In a preferred embodiment, the reduction in a symptom of inadequate myocardial function occurs within 2 weeks, and may occur within 1 week. In another preferred embodiment, remission occurs within 4 weeks; and, in yet another preferred embodiment, the serum LDL concentration achieved is less than 55 mg/dl.

In a related aspect, the invention features a medication for use in this or other methods, the medication including (a) a compound that includes eicosapentaeneoic acid or docosahexaeneoic acid (for example, a marine lipid) and (b) a cholesterol synthesis or transfer inhibitor.

In preferred embodiments of both of the above aspects, the compound that includes eicosapentaeneoic acid or docosahexaeneoic acid is administered at greater than or equal to 5 g/day; the marine lipid is a fish oil; the cholesterol synthesis or transfer inhibitor is administered at greater than or equal to 10 mg/day; the cholesterol synthesis or transfer inhibitor acts by inhibiting hydroxymethylglutarate (HMG) CoA reductase; and the cholesterol synthesis or transfer inhibitor is chosen from simvastatin, lovastatin, fluvastatin, or pravastatin. In other preferred embodiments, the method or medication further includes administering to the mammal any one or more of the following: niacin (for example, at 0.5–3 g/day); a bile acid sequestrant (for example, cholestyramine or colestipol, at, for example, between 5–20 g/day); aspirin (for example, at greater than or equal to 80 mg/day); and/or buspirone (for example, at between 10–80 mg/day).

The medication described above is useful for the treatment of a number of coronary diseases. For example, the medication may be used to treat inadequate myocardial function (for example, resulting in angina) or to reduce a coronary artery stenosis, preferably, by at least 20%. The medication may also be used to restore blood flow to infarcted myocardium or to improve myocardial function (for example, perfusion) without invasive revascularization of a coronary artery.

In a second aspect, the invention features a method for treating heart disease (for example, a coronary artery stenosis or a disease having angina as a symptom) in a mammal, that involves administering buspirone to the mammal in an amount which reduces a heart disease symptom (for example at between 10–80 mg/day).

In a third aspect, the invention features a method for reducing a coronary artery stenosis by at least 20%, that involves the administration of a cholesterol-lowering therapeutic, combined with dietary restrictions, whereby a serum LDL concentration of less than or equal to 70 mg/dl (preferably, 65 mg/dl, more preferably, 60 mg/dl, and, most preferably, 55 mg/dl) is achieved. In other related aspects, the invention features methods for restoring blood flow to infarcted myocardium; preventing a heart attack in a mammal at high risk due to coronary artery disease; reducing mortality due to an adverse cardiovascular event; or improving myocardial function, for example, perfusion (preferably, within 4 weeks, more preferably, within 2 weeks, and, most preferably within 1 week), without invasive revascularization of a coronary artery (for example, without physical manipulation of a coronary artery, such as by coronary bypass grafting or angioplasty), that involves the administration of (a) a compound that includes eicosapentaeneoic acid or docosahexaeneoic acid (for example, a marine lipid) and (b) a cholesterol-lowering therapeutic, combined with dietary restrictions, whereby a serum LDL concentration of less than or equal to 70 mg/dl (preferably, 65 mg/dl, more preferably, 60 mg/dl, and, most preferably, 55 mg/dl) is achieved. For these and all of the above methods, further reduction of serum LDL concentration is possible and may be beneficial.

In preferred embodiments, the above methods prevent coronary artery disease for greater than 5 years, and may prevent a disease for greater than 10 years; the compound including eicosapentaeneoic acid or docosahexaeneoic acid is administered at greater than or equal to 5 g/day; the cholesterol synthesis or transfer inhibitor is chosen from the group consisting of simvastatin, lovastatin, fluvastatin, and pravastatin; and a bile acid sequestrant, niacin, and/or aspirin is further administered to the mammal.

In other preferred embodiments of any of the methods of the invention, the dietary restrictions involve an intake of less than or equal to 10%, and preferably less than or equal to 5%, of calories (excluding fish oils) from dietary fat; and the cholesterol-lowering therapeutic involves (a) a compound that includes eicosapentaeneoic acid or docosahexaeneoic acid (for example, a marine lipid at, for example, greater than or equal to 5 g/day) and (b) a cholesterol synthesis or transfer inhibitor (for example, simvastatin, lovastatin, fluvastatin, or pravastatin), and may optionally include a bile acid sequestrant, niacin, and/or aspirin.

By "treating inadequate myocardial function" is meant, without limitation, reducing or relieving any one or more of the symptoms known in the art to be associated with inadequate myocardial function, including, without limitation, pain, pressure, tightness, or heaviness in the chest area; shortness of breath; heart palpitations; abrupt onset of weakness or fatigue; or lower jaw or neck pain. "Remission" of symptoms of inadequate myocardial function is considered to have occurred when a patient experiences less than one symptomatic episode (for example, those symptoms listed above) of inadequate myocardial function per week. "Complete remission" is considered to have occurred when a patient experiences less than one symptomatic episode (for example, those symptoms listed above) of inadequate myocardial function per six months.

By a "marine lipid" is meant any compound which includes eicosapentaeneoic or docosahexaeneoic acid or which is a lipid and is derived from or purified from a marine (i.e., salt water) animal, or which is synthesized based on such a naturally-occurring lipid. Preferred marine lipids are fish oils.

By a "cholesterol synthesis or transfer inhibitor" is meant any compound which retards or blocks the formation of cholesterol or its esters from non-cholesterol sources. Preferably, the inhibitor acts by inhibiting hydroxymethylglutarate (HMG) CoA reductase, but may, for example, also act by retarding the action of acetylcholesterol acyl transferase. Examples of cholesterol synthesis or transfer inhibitors include, without limitation, simvastatin, lovastatin, fluvastatin, and pravastatin.

By a "bile acid sequestrant" is meant any agent which retards or blocks the transport of bile acids from the intestine into the bloodstream. Examples include, without limitation, cholestyramine and colestipol.

By "infarcted myocardium" is meant cardiac tissue to which blood flow has been interrupted in a substantially irreversible manner.

By "invasive revascularization" is meant any revascularization which is accomplished by physical manipulation of the heart or coronary arteries including, without limitation, replacement or distension of vessels, or creation of new vascular channels by physical means. This term does not include revascularization which occurs solely as a result of the administration of pharmacological agents, or dietary or lifestyle changes.

By "stenosis" is meant any narrowing of a coronary artery, regardless of degree.

The methods and compositions of the present invention provide advantages over more traditional approaches to the treatment of heart diseases. These advantages include a reduction in the need for invasive revascularization with its associated morbidity and mortality, and the maintenance of an excellent quality of life and objective improvement in myocardial and peripheral perfusion. These advantages are particularly desirable because they allow for significant improvements in a patient's condition at minimal cost and with minimal physical and emotional trauma.

Other features and advantages of the invention will be apparent from the following detailed description thereof, and from the claims.

DETAILED DESCRIPTION

The invention features therapeutic methods and compositions for the rapid and enduring relief of inadequate myocardial function and for treatment of coronary artery disease. To more fully describe this invention, applicants present below a retrospective analysis of treatment records for a representative group of patients with severe coronary artery disease who have been treated with applicants' aggressive lipid and cholesterol management therapy. The protocol emphasizes dietary shunting of exogenous fats and oils to marine lipids, multifactorial cholesterol-lowering pharmacotherapy with a target serum LDL concentration of no more than 70 mg/dl (and preferably no more than 55 mg/dl), and adjunctive use of niacin and aspirin.

The consequences of the therapy are rapid and enduring relief of the symptoms of inadequate myocardial function (for example, angina), improved exercise tolerance, and objectively demonstrable improvement in myocardial perfusion. In addition to the myocardial changes, evidence of remission of peripheral atherosclerosis has been observed. In several cases, prompt and dramatic increases in cardiovascular status were documented, and none of the patients, to date, has suffered a known myocardial infarction. The outcomes, compared to historical controls and national records, suggest that this form of multifocal intervention outperforms surgical or invasive management of severe coronary artery disease.

The patient population in this study consisted of 11 individuals with severe coronary artery disease who were refractory to CABG or PCTA or who declined recommended CABG or PCTA, and one individual with severe carotid artery stenosis. The study group consisted of 10 men and 2 women, with a median age at entry into the program of 65 years (mean, 65.8 years), and a mean time in program of 4.1 years (range, 9 months to 12 years). In the 48.8 compliant patient-years, no myocardial infarcts, one stroke, and three deaths due to all causes were observed. One patient who remained compliant showed worsening of symptoms and eventually underwent bypass grafting. This patient initially presented with bilateral carotid stenosis, had a history of high alcohol consumption, and died of an esophageal neoplasm a year after engraftment and endarterectomy. For the purposes of analysis, the year following CABG was not considered to contribute to the patient years in the program, but the death was recorded as one of two observed among the population. Two individuals who were advised to pursue medical and dietary lifestyle modifications, but showed little evidence of compliance until worsening status compelled a significant change in behavior, were analyzed for the period during which they were judged to be compliant, as measured by the decline in their serum cholesterol concentration.

The mean serum LDL concentration of the population, 57 mg/dl (range, 42 to 74), was calculated from the individual means for each patient, which were obtained from a heterogeneous number of observations. In calculating the mean population LDL, the mean of each individual was given equal weight.

In this study, ten patients experienced angina at the time of presentation. The median time to remission of anginal symptoms was calculated on the basis of the nine patients who presented with angina and for whom records of anginal frequency were accessible. Remission, as used below, was defined as an anginal frequency of one episode per week or less, and the median time to remission was 4 weeks, range 2 to 24 (mean 6.33) weeks. One compliant patient developed angina despite good regulation of serum lipids.

Angiographic data indicated that the therapy described herein was capable of producing dramatic improvement in luminal diameter, with complete regression of plaque documented in one example. In a second case, nearly complete regression was observed in a patient with longstanding vascular disease.

Similarly, in one instance, single photon emission computed tomography (SPECT) of radiolabeled thallium uptake prior to program entry revealed a septal and inferoposterior infarction (i.e., completely dead muscle by scan) with significant periinfarction ischemia; reimaging ten months after program entry showed that the area of infarction had nearly completely resolved, with only minor ischemic changes remaining.

The following case reports document the effectiveness of this therapy.

Patient DR

Patient DR was a 40 year-old, 185 cm white male at the time he was hospitalized for acute myocardial infarction. Upon admission, he was found to have mild hypertension and was 14 Kg over an ideal weight of 76 Kg. His total serum cholesterol was 276 mg/dl. He had never smoked cigarettes and completed a cardiac stress test through Stage 5 of the Bruce protocol without abnormalities six months prior to admission. His hospital course was uneventful. Following discharge he had chest and back pain with minimal exertion. A stress test was strongly positive at 5 minutes of the Bruce protocol and a coronary angiogram two and a half months after the initial infarct showed a single high grade (95% stenosed) LAD lesion at the level of the first diagonal. The ejection fraction was normal (60%). Angioplasty 5 months after infarct gave symptomatic relief and reduced the LAD narrowing from 95% to 22%. The serum cholesterol was 267 mg/dl. Angina recurred in three months, and a repeat angioplasty 9 months after admission reduced the stenosis from 95% to 30%. The serum cholesterol was 276 mg/dl. Angina recurred in three months, and a third angioplasty 13 months post-infarct reduced the narrowing from 91% to 21%. Total serum cholesterol was 254 mg/dl, and the patient was started on medical therapy.

Fat intake was limited to 5–8 g/day, almost all dietary cholesterol was avoided, 4 g/day of niacin was taken in divided doses, and 16 g of cholestyramine were consumed with meals. Medical therapy also included 50 mg of atenolol and 80 mg of aspirin per day. One month after initiation of therapy, the total cholesterol was 136 mg/dl and the HDL cholesterol 48 mg/dl. The patient was advised to maintain total cholesterol below 120 mg/dl, to lose weight, and to spend 30 minutes a day exercising. The exercise consisted of vigorous rowing for 30 minutes a day for three days a week and of walking briskly on the days that he didn't row. In 4 months he shed 16 kg. Six months after initiation of therapy, the total cholesterol was 116 mg/dl. At that time a thallium stress was normal at Stage 5 of the Bruce protocol, and an angiogram a month later showed residual stenosis of 26%. Over the next 5 years, the patient adhered to the regimen, and the total cholesterol varied from 116 to 134 mg/dl. Angiography at six and a half years post infarct showed no stenosis and no evidence of coronary artery disease. Relaxation of diet had prompt consequences, with the total cholesterol rising to 146 mg/dl within a week. A year later the total serum cholesterol had remained at the same level, and he had regained 3 of the 16 kg he lost, the HDL cholesterol was 60 mg/dl, the LDL 74 mg/dl, and triglycerides 84 mg/dl. At 12 years post-infarct, he is asymptomatic and appears healthy.

Patient RS

At the time of initiation of therapy, RS was an 81 year-old, 168 cm, 85 kg white male with a 12 year history of severe coronary disease dating to his first admission for unstable angina. He denied use of cigarettes and had no history of hypertension.

Twelve years prior to therapy, he had an inferolateral wall myocardial infarction which was estimated to have affected approximately one quarter of the myocardial mass. He had another myocardial infarction 11 years later and a week later underwent CABG with anastomosis of the internal mammary artery to the left anterior descending artery and a bypass of the right coronary artery. It was noted at that time that he had hypokinesis of the inferior wall of the heart. Thirteen months later he had angioplasty of the left circumflex. Three months later he had angioplasty of the restenosed left circumflex and of the now stenosed distal part of the graft bypassing the right coronary lesion.

Three months after the second angioplasty, a thallium stress test that was markedly positive after 4½ minutes of exercise following the Bruce protocol. The test was terminated due to dyspnea and fatigue. The maximum heart rate was 122 bpm, and the maximum blood pressure was 124/60, with a double product of 15,000. No chest pain or arrhythmia occurred. Pseudonormalization of inverted T waves in V4 thru V6 occurred at peak exercise. There was increased lung uptake of the thallium, and decreased label in the lateral wall which nearly completely redistributed on delayed imaging. Reduced radioactivity was observed in the inferobasal myocardium which persisted on delayed imaging with minor redistribution around the perimeter. The interpretation was an inferobasal myocardial infarction with peri-infarction ischemia, lateral wall ischemia, and exertional LV dysfunction at a low cardiovascular work load. An angiogram taken after the stress test showed a 95% focal restenosis of the previously dilated proximal circumflex and a 70% restenosis of the distal right coronary graft. The proximal left anterior descending was severely and diffusely diseased with numerous areas narrowed by greater than 90%. The internal mammary artery was widely patent, and there was good run-off into the distal left anterior descending and retrograde filling of part of the proximal left anterior descending and two of its diagonals. The left main coronary artery showed intimal irregularities. The right coronary artery was diffusely diseased in its proximal third and narrowed in several areas to 40–50%. It was completely occluded after a large right atrial branch.

On examination the patient weighed 84.5 kg (17.5 kg in excess of ideal). The heart was enlarged, with a grade 3/6 systolic murmur. Neck veins were not distended, and there was no ankle edema. There were no bruits in the neck. The fundi were normal. His medications consisted of diltiazem 60 mg q.i.d., propranolol 10 mg q.i.d., dipyridamole 25 mg b.i.d., and nitroglycerin patches as needed, which was daily. The total cholesterol was 188 mg/dl, HDL 44 mg/dl, LDL 115 mg/dl, triglycerides 147 mg/dl, fibrinogen 404 mg/dl, and the ratio of total to HDL cholesterol was 4.3. The apolipoprotein A1 was 100 mg/dl, the apoliporotein B was 75 mg/dl, and the serum glucose was 134 mg/dl. The patient reported angina (pain over the left chest and shortness of breath) so severe that he had difficulty walking 50 meters from his house to the mailbox, even pausing to rest en route.

Initial therapy consisted of 40 mg/day lovastatin, 80 mg per day aspirin, 100 mg q.i.d. niacin, and 5 g/day fish oil. He was advised to lose weight and spend 15–30 minutes per day walking at a gentle pace. It was also recommended that he limit fat intake to 5–8 g per day, to continue diltiazem 60 mg q.i.d., to replace dipyridamole with 80 mg of aspirin once a day, and to discontinue the use of transdermal nitroglycerin. Three weeks after initiation of therapy, 10 mg q.i.d. propranolol was replaced with 25 mg atenolol once a day.

At the end of one week of therapy, the total cholesterol was 118 mg/dl, the HDL 40 mg/dl, the LDL 52 mg/dl, the triglycerides 132 mg/dl, and the fibrinogen 419 mg/dl. The fish oil was increased to 15 g per day, the niacin gradually increased to 3.0 g/day by the end of the next week. Psyllium, 3.5 g twice a day, was added to the regimen. Three weeks after the initial visit the total cholesterol was 66 mg/dl, the HDL was 36, the LDL 20, the triglycerides 49, and the fibrinogen 315. At this time he was able to walk two miles without angina. Psyllium was increased to 3.5 g three times a day because of constipation. After 5 weeks of treatment, the total cholesterol was 69 mg/dl, HDL 42, LDL 18, triglycerides 43, fibrinogen 211. The serum liver enzyme concentrations were normal, and his serum glucose had risen to 161 mg/dl. He reported some mild angina during a daily two mile walk. During the next two weeks, he had some itching and flushing from the niacin and decreased the dose to 1.5 g/day. In the ninth week he reported dancing until 3 a.m. on New Year's Eve.

Over the next year, his regimen stayed the same, with minor dietary modifications. During that time, the total cholesterol averaged 98 mg/dl (range 90–114), the HDL 42 (33–55), the LDL 42 (16–70), the serum triglycerides 71 (57–94), and fibrinogen 341 (253–482). In September of that year, he reported mild angina after carrying a 23 kg load 200 meters. He had four more mild episodes of angina in September and October. One occurred during an episode of emotional agitation and the others during heavy exertion. In November an attempt was made to substitute lisinopril (5 mg/day) for diltiazem (60 mg four times a day). Angina recurred with mild to moderate exercise. After one month the lisinopril was stopped and diltiazem restarted, with prompt remission of angina. Seven months after initiation of therapy, an ambulatory cardiac monitoring for silent ischemia was negative. One year after initiation of therapy, an ultrasound examination of the carotid arteries revealed plaque on the posterior wall of the right carotid bifurcation which was 1.5 cm long and about 0.4 cm deep. The left side was free of plaque.

At the beginning of the second year of therapy, the serum globulin levels were found to be slightly elevated as a result of a monoclonal gammopathy with an IgG kappa protein. A bone marrow biopsy showed 8% plasmacytes (normal 0-1). The plasma cells did not appear in sheets and the biopsy was not considered diagnostic of a plasma cell dyscrasia. Iron stores were decreased. The blood hemoglobin level was normal at 13.0 g/dl as was the white blood cell count at 9,600 per μl and the platelet count at 387,000 per μl. Fifteen and sixteen months after initiation of therapy, he noted some angina when he exercised in cold weather. Nineteen months after initiation, he complained of fatigue and difficulty sleeping. He was given trazodone (50 mg) and imipramine (25 mg) at bedtime with fair to moderate relief. A month later, imipramine was increased to 50 mg a day, and this was continued, with minor interruptions, throughout the year. A repeat ultrasound examination of the carotid arteries showed no change over the examination of the previous year. Nasal allergies recurred and were treated with beclomethasone and cromolyn sodium nasal sprays.

In the fall of that year, he vacationed in Europe for 10 days, spending part of the time at high altitude in the Alps. He abandoned his diet, consumed a substantial amount of salt, and developed congestive heart failure and atrial fibrillation. On return, he was given furosemide 40 mg twice a day, digoxin 0.25 mg, and warfarin 5 mg once a day. The congestive heart failure cleared in 24 hours, and within six days he spontaneously reverted to sinus rhythm and the warfarin was stopped.

In December, he shoveled 15 cm of snow off a 50 meter driveway without discomfort. In a treadmill stress test according to the Bruce protocol, he achieved a heart rate of 144 and a blood pressure of 128/70 at the end of 6 minutes (double product 18,000). There was no angina and no arrhythmia and minimal depression of the ST segments in the lateral leads during recovery. There were no changes in the T waves. At the end of December, he weighed 78 kg.

Two adverse events occurred during the third year of therapy. The first was the development of congestive heart failure during a spring ski trip at high altitude (2.2 km) during which he stopped taking furosemide on his own initiative. The resulting heart failure cleared promptly with diuresis and two days of hospitalization. A month later, (2½ years after the start of therapy), he had a repeat thallium stress test in which he exercised for 7 minutes and reached a heart rate of 130 and a double product of 21,000. The scan showed abnormal lung uptake and mild ventricular dilatation. There was a large area of diminished perfusion in the inferior and inferolateral walls on the stress image with fill-in on the resting image. The interpretation was that of a large area of moderate ischemia in the inferior and inerolateral walls of the left ventricle.

The second adverse event was a stroke in the late summer affecting the left middle cerebral artery which left him with a partially paralyzed right arm and partial aphasia. Six blood samples taken prior to the stroke gave an average total cholesterol of 121 mg/dl (range 109–138), an HDL of 38 (range 24–47), serum triglycerides of 59 mg/dl (47–80), fibrinogen of 386 (292–560), and a mean LDL of 71 mg/dl. During hospitalization for the stroke, echocardiography showed a large left atrium (4.5 cm; normal 1.9–4.0 cm), a large left ventricle—diastolic dimension (6.0 cm; normal 3.7–5.5 cm), increased left ventricular wall thickness—septal wall (1.3 cm; normal 0.6–1.1 cm)—posterior wall (1.2 cm; normal 0.7–1.1 cm), and decreased ejection fraction (30–35%). Overall left ventricular function was moderately reduced in all areas but was somewhat worse in the posterior wall. The aortic valve was calcified, and there was slightly reduced excursion. The mitral valve was normal, but there was annular mitral calcification and mild to moderate mitral regurgitation. No thrombus was seen. By the end of the year he had made a partial recovery from the stroke, with some residual slurring of speech and weakness in the right arm. In the fourth year of therapy, his serum cholesterol continued to be well controlled, and he exhibited no additional signs of coronary artery disease. However he continued to show signs of poor adjustment to the consequences of the stroke, his mental status declined markedly, and he eventually succumbed to aspiration pneumonia.

Patient MS

Patient MS, a white female, 59 at the time of initiation of therapy, presented with recurrent angina, averaging 4 to 5 episodes a day. In the year prior to initiation of therapy, her serum cholesterol averaged 222 mg/dl (range 198 to 247), triglycerides 138 mg/dl (range 121 to 160), HDL cholesterol 35 mg/dl (range 34 to 36), and LDL cholesterol 146 mg/dl (range 138 to 154). Coronary angiography showed severe narrowing of the left anterior descending and circumflex arteries, with stenosis of the right coronary artery after the first branch. A thallium stress test showed poor perfusion of the posterolateral myocardium, and echo arteriography showed 90% stenosis of the left common carotid, moderate stenosis of the origin of the left vertebral artery, and stenosis of both subclavian arteries. A blood pressure measurement could not be completed in the left arm because a pulse could not be detected.

Initial therapy consisted of 40 mg per day of lovastatin, 80 mg per day of aspirin, 3 g per day of niacin, and 10 g per day of fish oil, and a suggested diet containing less than 10% of calories from fat. Within two weeks, the total cholesterol was 109, the HDL 52, the LDL 51, and the triglycerides 32 mg/dl. Marked improvement of angina symptoms were noted, although some episodes of nocturnal angina occurred during the following two months. Over the five months following initiation of therapy, 11 measurements of total serum cholesterol averaged 112 mg/dl, range 82 to 143. Stress tests at 2 and 5 months post-induction showed ST segment depression of 1.2 and 0.9 mm respectively; no angina was noted during the conduct of the test. Niacin intolerance appeared, and the dose was decreased to 1 g per day. The fish oil was increased to 15 g per day. Over the next three years, 36 measurements showed a mean total cholesterol of 118 mg/dl (range 82 to 152), and a mean HDL of 43 (range 33 to 56). At 18 months it was possible to measure blood pressure with a cuff positioned over the left arm. The patient was followed less closely over the fourth year for reasons unrelated to the therapy and in the fifth year was seen only three times, again because of problems unrelated to a willingness to continue. During the fifth year, she discontinued the lovastatin, and the total cholesterol rose to 176 mg/dl, range 155 to 194. During the sixth year, she resumed therapy, and four measurements showed the total cholesterol to average 134 mg/dl (range 118 to 145).

Apart from occasional episodes of angina during the first two months of therapy, the patient reported no discomfort suggestive of angina except on three occasions, the first occurring 15 months after induction of therapy, when she reported two episodes of left neck pain originating under the angle of the jaw over the left common carotid and radiating to the left axilla. The left neck pain was relieved by administration of nitroglycerin and did not subsequently recur. Eighteen months after inception she reported a burning pain across the upper chest during a walk after eating. Twenty-five months after induction of therapy, she reported an episode of mild angina upon exertion in the cold.

Patient JRS

Patient JRS, a white male, 58 at the time of initiation of therapy, presented with a strongly positive thallium perfusion stress test, partial stenosis of the carotid arteries as determined by echo arteriography, and angina. The mean of four serum cholesterol determinations prior to treatment was 181 mg/dl, range 159 to 204. Simvastatin, 20 mg per day, aspirin, 80 mg per day, niacin, 3 g per day, and fish oil, 12 g per day, were initially administered, and a diet of less than 10% of calories from fat was recommended. Within a month of therapy the total cholesterol was 108 mg/dl and marked relief from angina symptoms was noted. Over the following year the niacin was varied between 3 g and 1 g per day, and a maintenance regimen of 2 g per day of niacin, 40 mg per day of simvastatin, and 10 g per day of fish oil was established. Seventeen measurements over the course of a year gave a mean serum cholesterol of 103 mg/dl, range 75 to 131, a mean serum HDL cholesterol of 41 mg/dl, range 31 to 49, and a mean LDL concentration of 60 mg/dl, range 28–73. During this period the patient reported feeling chest tightness once during strenuous exercise on a treadmill, but otherwise did not complain of symptoms suggestive of angina following exertion. However tightness in the chest accompanying situations that provoked anxiety or distress continued to recur. Buspirone, 10 mg b.i.d., was added to his medications, and no further episodes of chest tightness were reported.

Patient JE

Patient JE was first seen at the age of 62 and was observed to have a serum total cholesterol concentration of 237 mg/dl. He was advised to attempt to lower his cholesterol level with diet and medication, but declined medical treatment. Two years later he complained of angina and in the third year agreed to try medical treatment, which consisted of colestipol, 12 g per day. His serum total cholesterol declined from a mean of three determinations of 241 mg/dl to a mean of three determinations of 217 mg/dl. The severity of his angina declined, and he discontinued the medication. Seven years after his initial visit, he continued to have intermittent exertional angina and agreed to attempt to reduce his serum cholesterol. Therapy consisted of fish oil, 6 g per day, lovastatin, 20 mg per day, aspirin, 80 mg per day, and niacin, 3 g per day. His total cholesterol fell to 183 (mean of three determinations), his angina remitted, and he discontinued lovastatin and niacin. Ten years after the initial visit, echo arteriography showed narrowing of the carotids, and he resumed niacin, 2 g per day, and fish oil, 3 g per day. For four years the patient continued to be weakly compliant, with serum cholesterol concentrations ranging from 169 to 212 mg/dl. Fifteen years after the initial visit, the patient complained of angina while walking up a seven degree incline. Three months later he complained of angina at rest and underwent PCTA in January. Three months later he underwent repeat PCTA. Three months later he again suffered angina at rest and underwent five vessel CABG. Two months later unstable angina recurred, and angiography revealed stenosis of four of five vessel grafts. He underwent PCTA twice and was proposed for repeat CABG. During this period the patient became relatively compliant, with total cholesterol ranging between 115 and 142 mg/dl. However he continued to experience nonexertional angina which was refractory to transdermal nitroglycerin. Buspirone, 15 mg t.i.d., was added to his medications, which were brought to 6 g per day of fish oil, 10 mg per day of simvastatin, 12 g per day of colestipol, 1.5 g per day of niacin, isosorbide dinitrate, 40 mg t.i.d., and daily transdermal nitroglycerin. During the induction phase, his angina remitted, but discontinuation of the nitroglycerin resulted in five episodes of angina. The patient was advised to continue to employ sublingual nitroglycerin as needed. The buspirone dosage was increased to 20 mg t.i.d., and the isosorbide dinitrate was discontinued. Marked palliation of the symptoms was observed, and the patient reported one episode of mild angina in two weeks with no use of nitroglycerin. In December he reported two episodes of angina and through June of the next year, no episodes of angina. In 1996 his total cholesterol averaged 118 mg/dl, his HDL 63 mg/dl, and his LDL 43 mg/dl.

Patient PR

Patient PR, a Caucasian male, underwent CABG at the age of 68. Two years later marked stenosis of the carotid arteries was noted, and a month later the patient agreed to begin medical therapy. From an initial mean total cholesterol of 231 mg/dl (three determinations, range 224–239), the combined use of fish oil, 9 g per day, aspirin, 80 mg per day, niacin, 1.5 g per day, pravastatin, 20 to 40 mg per day, and colestipol, 10 g per day, produced a modest improvement in serum total cholesterol (159 mg/dl, mean of 11 determinations). Forty-four months after CABG, he developed unstable angina and a thallium stress test was strongly positive. Coronary angiography disclosed severe narrowing of four vessels, with an ejection fraction of 40%. He was advised to undergo a second CABG. He elected instead to adhere more rigorously to the dietary guidelines initially set out for him. Over the six months subsequent, his serum total cholesterol averaged 109 mg/dl, range 96–121, his HDL 25, range 17–31, and his LDL 69, range 62–77, on a medical regimen consisting of fish oil concentrate, 6 g per day, simvastatin, 40 mg per day, and niacin in amounts ranging from 0.3 g to 1.5 g per day. Although the frequency and severity of anginal episodes declined, he continued to experience angina at rest and buspirone, 30 mg per day, was added to the medications. After one month the buspirone dosage was increased to 15 mg t.i.d. During this time the severity of his symptoms declined markedly, from pain to mild tightness, but the frequency remained approximately constant. Six months after initiation of therapy, his anginal symptoms resolved completely. In the first six months of the following year, his total cholesterol averaged 122 mg/dl, the HDL 37 mg/dl, and the LDL 72 mg/dl. Toward the end of the period, he reported one fainting episode and was evaluated for cardiac dysfunction. The sudden onset was suggestive of arrhythmia but hypoglycemia could not be ruled out. An ECG performed at that time was normal. Shortly, thereafter, the patient expired suddenly, and an autopsy was not performed.

Patient HM

Patient HM presented at age 67 with a strongly positive thallium stress test with evidence of reversible septal, apical, and anterolateral ischemia, angiographic evidence of coronary artery disease with total occlusion of the proximal LAD, a high grade obstruction of the origin of a major diagonal branch supplying most of the anterior precordium, a fairly high grade stenosis of the circumflex, and a moderate lesion near the origin of the right coronary artery. At the time of testing, he provided a history of angina pectoris of at least four years duration, with recent exacerbation such that symptoms appeared after large meals or a short walk. He was recommended to undergo CABG but elected to pursue medical therapy instead. Prior to entry into the program, his mean total cholesterol was 243 mg/dl, and his mean HDL was 45 mg/dl, average of two determinations. His initial medical therapy was titrated up to the following dosages: fish oil, 5 g per day, lovastatin, 40 mg per day, cholestyramine, 4 g per day, aspirin, 80 mg per day, and niacin, between 0.3 and 0.5 g per day. Within a month of therapy, he reported substantial palliation of angina symptoms. Over the following year, he reported angina attacks with an average frequency of twice per month. During this period the cholestyramine was discontinued, and the niacin was increased to 1 g per day. Pravastatin, 40 mg per day, replaced lovastatin at the same dosage for a four month period with little discernible change in serum lipids. He continued to do well with the regimen for 29 months, when he discontinued the use of fish oil. Four months later he began to experience angina, and the frequency and severity increased over the following three months. He was urged to resume consumption of fish oil and saw a marked palliation of symptoms within a month. Thereafter the frequency of reported anginal episodes declined to approximately two episodes per month. Over the most recent two years, 23 determinations have given a mean total cholesterol of 114 mg/dl, range 92 to 137, and a mean HDL cholesterol of 47 mg/dl, range 31 to 52. His average total cholesterol for 1995 was 118 mg/dl, his HDL 41 mg/dl, and his LDL 68 mg/dl.

Patient CJ

Patient CJ was a 65 year old Caucasian male who had undergone two courses of angioplasty without relief of angina. At the time of initiation of therapy, his serum cholesterol averaged 200 mg/dl (four determinations, range 173–214), and his HDL cholesterol averaged 48 mg/dl (range 42–54). He experienced symptoms of angina while walking. Initial treatment consisted of fish oil, 10 g per day, lovastatin, 10 mg per day, aspirin, 80 mg per day, and niacin, 2 g per day. Within a month he reported no angina while playing tennis, golf, or walking. However he did report one episode of chest tightness under emotional duress. During this phase his serum total cholesterol was 140 mg/dl (range 136–152), mean of 7 determinations. Over a three month period, the lovastatin dosage was increased to 30 mg per day, and he remained on this regimen for 18 months, during which period 18 determinations of serum total cholesterol yielded a mean of 137 mg/dl, range 100–169, and a mean HDL cholesterol of 73, range 64–89. He experienced mild conjunctivitis of unknown etiology and pravastatin, 10 mg per day, was substituted for lovastatin. Over the next 13 months, 11 determinations of serum cholesterol yielded a mean of 152 mg/dl (range 136–184). During this period he reported one instance of mild angina. After a brief transitional period, simvastatin, 40 mg per day, was substituted for pravastatin. A mean of five determinations yielded a serum total cholesterol of 118 mg/dl (range 81–146), and HDL cholesterol of 55 mg/dl (range 37–71). For the year of 1995 his total cholesterol was 121, HDL was 82, and LDL was 53, triglycerides 44 mg/dl. His last report of angina was approximately four years ago.

Patient TG

Patient TG presented at the age of 78 with a history of two myocardial infarctions, one at the age of 50 and the other at the age of 64. Carotid ultrasonography showed significant narrowing of both arteries. At the time of initiation of therapy, his serum cholesterol was 235 mg/dl. Initial treatment consisted of fish oil, 12 g per day, pravastatin, 20 mg per day, aspirin, 80 mg per day, and niacin, 3 g per day. Fifteen determinations of serum total cholesterol in the first year gave a mean of 116 mg/dl, range 99–133, a mean serum HDL cholesterol of 67, range 47 to 94, and a mean LDL cholesterol of 42, range 33–54 mg/dl. Over the course of therapy, however, no diminution of the carotid stenosis was noted, and despite clear evidence of compliance, two years after entry into the program he developed angina and was referred for coronary artery bypass grafting and carotid endarterectomy. A year later he died of an esophageal tumor.

Patient MAM

Patient MAM presented as a Caucasian female, 77, with daily angina and a strongly positive thallium stress test. Her initial medications consisted of fish oil, 6 to 12 g per day, pravastatin, 10 mg per day, aspirin, 80 mg per day, and niacin, 3.5 g per day. Within six weeks of initiation of therapy, the frequency of anginal attacks declined to once per two weeks, and thereafter to zero. No subsequent attacks were observed for the following 33 months (up to present). A repeat thallium stress test administered 13 months after the initial exam showed improved perfusion. Over the first year, ten determinations gave a mean serum cholesterol of 125 mg/dl, range 108–144, a mean HDL of 77, range 57–84, and a mean LDL of 41, range 29–55. In the most recent year, on a regimen of 4 g per day of fish oil, 10 mg per day of pravastatin, and 2 g per day of niacin, the serum cholesterol averaged 154 mg/dl (range 142 to 164, 6 determinations), the HDL cholesterol averaged 92 mg/dl (range 80–108), and the LDL averaged 51 (range 44–56).

Patient CR

Patient CR, a 64 year old white male at the time of entry, was referred to the program after several episodes of chest pain and shortness of breath led to evaluation for possible coronary artery disease. A thallium stress test showed a septal and inferoposterior infarction with significant periinfarction ischemia and 1.5 mm ST segment depression in leads V5 and V6 at stage IV of the Bruce protocol, when the test was terminated because of fatigue. Echo arteriography revealed plaque in both bulbs: a soft 4 mm plaque in the bulb of the right common carotid and a 2.3 mm plaque in the left bulb. In addition the right internal carotid had 2.6 mm plaque. The narrowing was not considered significant and flow velocities and spectral patterns were normal. When seen initially the patient complained of chest discomfort and shortness of breath on exertion. His mean serum cholesterol was 235 mg/dl. Medical therapy consisted of fish oil, 16 g per day, simvastatin, 40 mg per day, aspirin, 80 mg per day, and niacin, between 1.5 and 3 g per day. Nineteen determinations after initiation of treatment showed the mean total cholesterol to be 135 mg/dl, the mean HDL cholesterol to be 63 mg/dl, and the mean LDL cholesterol to be 54 mg/dl. The shortness of breath and chest pain symptoms resolved within two weeks without recurrence. However an episode of dizziness prompted him to seek re-evaluation 10 months after his referral. The second thallium stress test revealed a very minute inferoposterior and septal ischemia. No evidence of the original infarct was found. The stress test was terminated at stage VI due to fatigue; a heart rate of 183 was achieved. No ST segment depression was observed. A carotid ultrasound examination 11 months after the initial examination showed mild intimal thickening of both common carotids and a region of calcified plaque in the right bulb of 3.7 mm. The other two plaques had disappeared.

Patient KS

Patient KS was initially seen at age 49 and was counseled at that time to try to control his serum cholesterol concentration. He remained largely noncompliant, however, until the age of 57 when an episode of chest pain, a strongly positive thallium stress test, and an angiogram revealing serious disease with complete obstruction of the left anterior descending coronary artery prompted reconsideration. He declined surgical management and elected to undergo medical therapy. His serum total cholesterol fell from an average of 233 (mean of 21 determinations) without treatment to 124 (mean of 34 determinations). His current medications include colestipol, 20 g per day, simvastatin, 40 mg per day, and aspirin, 80 mg per day. In the most recent year his mean total cholesterol was 133, the mean HDL was 55, and the mean LDL was 64 mg/dl. Four years after testing disclosed serious disease he remains asymptomatic.

Summary of Results

From results obtained to date including those described above, the features of the claimed treatment which correlate best with rapid and enduring relief of inadequate myocardial function consist of aggressive lipid management, including a diet low in exogenous fats, supplemented with modest levels (5–15 g) of fish oils or related concentrates; niacin to raise HDL cholesterol; and blockade of formation of cholesterol at the level of hydroxymethylglutarate (HMG) CoA reductase, or, if necessary or desirable, prevention of bile acid resorption through bile acid sequestrants. In addition, the use of buspirone has proven effective in providing relief from refractory unstable angina. The evidence summarized here suggests that the palliative action of buspirone may be mediated principally through its effects on cardiovascular rheology. However, it is also possible that some fraction of the beneficial effect of buspirone is attributable to its well-defined action as an anxiolytic.

The methods and compositions of the present invention may be used to reduce the symptoms of inadequate myocardial function in any mammal, including humans, domestic pets, and livestock.

Other embodiments are within the claims.

What is claimed is:

1. A method for reducing coronary artery stenosis by at least 20% in a mammal comprising the administration to said mammal of a combination of (a) a composition comprising eicosapentaeneoic acid or docosahexaeneoic acid and (b) a cholesterol synthesis or transfer inhibitor, in combination with limiting fat or cholesterol intake, whereby a serum LDL concentration of less than or equal to 70 mg/dl is achieved.

2. The method of claim 1, wherein said serum LDL concentration achieved is less than 55 mg/dl.

3. The method of claim 1, wherein said combination further comprises niacin.

4. The method of claim 1, wherein said combination further comprises aspirin.

5. The method of claim 1, wherein said composition comprising eicosapentaeneoic acid or docosahexaeneoic acid is administered at greater than or equal to 5 g/day.

6. The method of claim 1, wherein said composition is a marine lipid.

7. The method of claim 6, wherein said marine lipid is a fish oil.

8. The method of claim 1, wherein said cholesterol synthesis or transfer inhibitor is administered at greater than or equal to 10 mg/day.

9. The method of claim 1, wherein said cholesterol synthesis or transfer inhibitor acts by inhibiting hydroxymethylglutarate (HMG) CoA reductase.

10. The method of claim 1, wherein said cholesterol synthesis or transfer inhibitor is chosen from the group consisting of simvastatin, lovastatin, fluvastatin, and pravastatin.

11. The method of claim 3, wherein said niacin is administered at between 0.5–3 g/day.

12. The method of claim 4, wherein said aspirin is administered at greater than or equal to 80 mg/day.

13. The method of claim 1, wherein said method further comprises administering to said mammal a bile acid sequestrant.

14. The method of claim 13, wherein said sequestrant is administered at between 5–20 g/day.

15. The method of claim 13, wherein said sequestrant is chosen from cholestyramine or colestipol.

16. The method of claim 1, wherein said method further comprises administering to said mammal buspirone.

17. The method of claim 16, wherein said buspirone is administered at between 10–80 mg/day.

* * * * *

UNITED STATES PATENT AND TRADEMARK OFFICE
CERTIFICATE OF CORRECTION

PATENT NO. : 7,109,206 B2
APPLICATION NO. : 09/735024
DATED : September 19, 2006
INVENTOR(S) : Brian Seed et al.

It is certified that error appears in the above-identified patent and that said Letters Patent is hereby corrected as shown below:

Column 7, Line 35, replace "apoliporotein B" with --apolipoprotein B--.

Column 9, Line 4, replace "inerolateral" with --inferolateral--.

Signed and Sealed this

Ninth Day of January, 2007

JON W. DUDAS
*Director of the United States Patent and Trademark Office*